(12) United States Patent
Brodbeck et al.

(10) Patent No.: US 7,491,328 B2
(45) Date of Patent: Feb. 17, 2009

(54) FUEL SAMPLER/STRAINER ASSEMBLY

(76) Inventors: Robert M. Brodbeck, 9310 S. Watson Gulch Rd., Littleton, CO (US) 80127; Charles A. Teilborg, 11452 SR 211, Usk, WA (US) 99180

( * ) Notice: Subject to any disclaimer, the term of this patent is extended or adjusted under 35 U.S.C. 154(b) by 2 days.

(21) Appl. No.: 11/668,595

(22) Filed: Jan. 30, 2007

(65) Prior Publication Data

US 2008/0178664 A1 Jul. 31, 2008

(51) Int. Cl.
*B01D 35/02* (2006.01)
*B67D 5/58* (2006.01)
*B01D 35/34* (2006.01)

(52) U.S. Cl. .............. 210/232; 210/464; 210/466; 210/469; 210/473; 210/244; 222/189.06; 222/189.07

(58) Field of Classification Search .............. None
See application file for complete search history.

(56) References Cited

U.S. PATENT DOCUMENTS

| | | | | |
|---|---|---|---|---|
| 242,962 | A * | 6/1881 | Newton | 222/189.07 |
| 1,641,051 | A * | 8/1927 | Rheney | 210/466 |
| 2,370,668 | A * | 3/1945 | Johnson | 222/189.07 |
| 2,556,627 | A * | 6/1951 | Miksis | 222/568 |
| 3,010,583 | A | 11/1961 | Kenyon | |
| 3,011,349 | A | 12/1961 | Kratz | |
| 3,063,289 | A | 11/1962 | Moul | |
| 3,503,250 | A | 3/1970 | Cotton | |
| 3,976,572 | A | 8/1976 | Reick | |
| 4,700,580 | A * | 10/1987 | Kamin | 73/864.51 |
| 4,956,298 | A | 9/1990 | Wagensteig | |
| 4,967,595 | A * | 11/1990 | Olson | 73/440 |
| 5,045,195 | A * | 9/1991 | Spangrud et al. | 210/266 |
| 5,359,905 | A | 11/1994 | Brodbeck | |
| 5,804,082 | A * | 9/1998 | Lowery, Jr. | 210/800 |
| 5,984,141 | A * | 11/1999 | Gibler | 222/80 |
| 6,076,704 | A * | 6/2000 | Weiler et al. | 222/83 |
| 6,126,048 | A * | 10/2000 | Bublitz | 222/570 |

(Continued)

OTHER PUBLICATIONS

Wing Arrow Products, Inc.; The GATS Jar—Instruction Manual (4 pages) 1.800.942.9464, no date.

*Primary Examiner*—Krishnan S Menon
*Assistant Examiner*—Madeline Gonzalez
(74) *Attorney, Agent, or Firm*—Lawrence N. Ginsberg

(57) ABSTRACT

The fuel sampler/strainer assembly includes a housing formed of fuel resistant material including a transparent elongated main body, a fuel receiving portion at an upper end thereof, and a fuel exiting portion also at the upper end thereof. The elongated main body has a closed lower end. The fuel receiving portion is generally tubular and has spaced-apart indentations in its upper end edge for alignment and cooperation with associated actuating arms of a pet cock drain valve. A rod is removably attachable at a first end to the fuel receiving portion and extends along a central axis of the fuel receiving portion and beyond the upper end edge of the fuel receiving portion so as to engage and manipulate a ball and spring drain valve at a second end of the rod. The fuel exiting portion includes a filter screen functioning as a barrier to water and desired particulate debris. A first protective cap fits over the fuel receiving portion for containing evaporative fumes while the fuel sampler/strainer assembly is being stowed. A second protective cap fits over the fuel exiting portion for similar purposes.

11 Claims, 3 Drawing Sheets

U.S. PATENT DOCUMENTS

| | | | |
|---|---|---|---|
| 6,344,146 B1 * | 2/2002 | Moorehead et al. | 210/668 |
| 6,357,602 B2 * | 3/2002 | Rutledge et al. | 210/477 |
| 6,858,134 B2 * | 2/2005 | Yates | 210/167.01 |
| 6,929,135 B1 * | 8/2005 | Hajianpour | 215/229 |
| 6,991,724 B2 | 1/2006 | Brodbeck | |
| 2005/0109688 A1 * | 5/2005 | Brodbeck et al. | 210/232 |

* cited by examiner

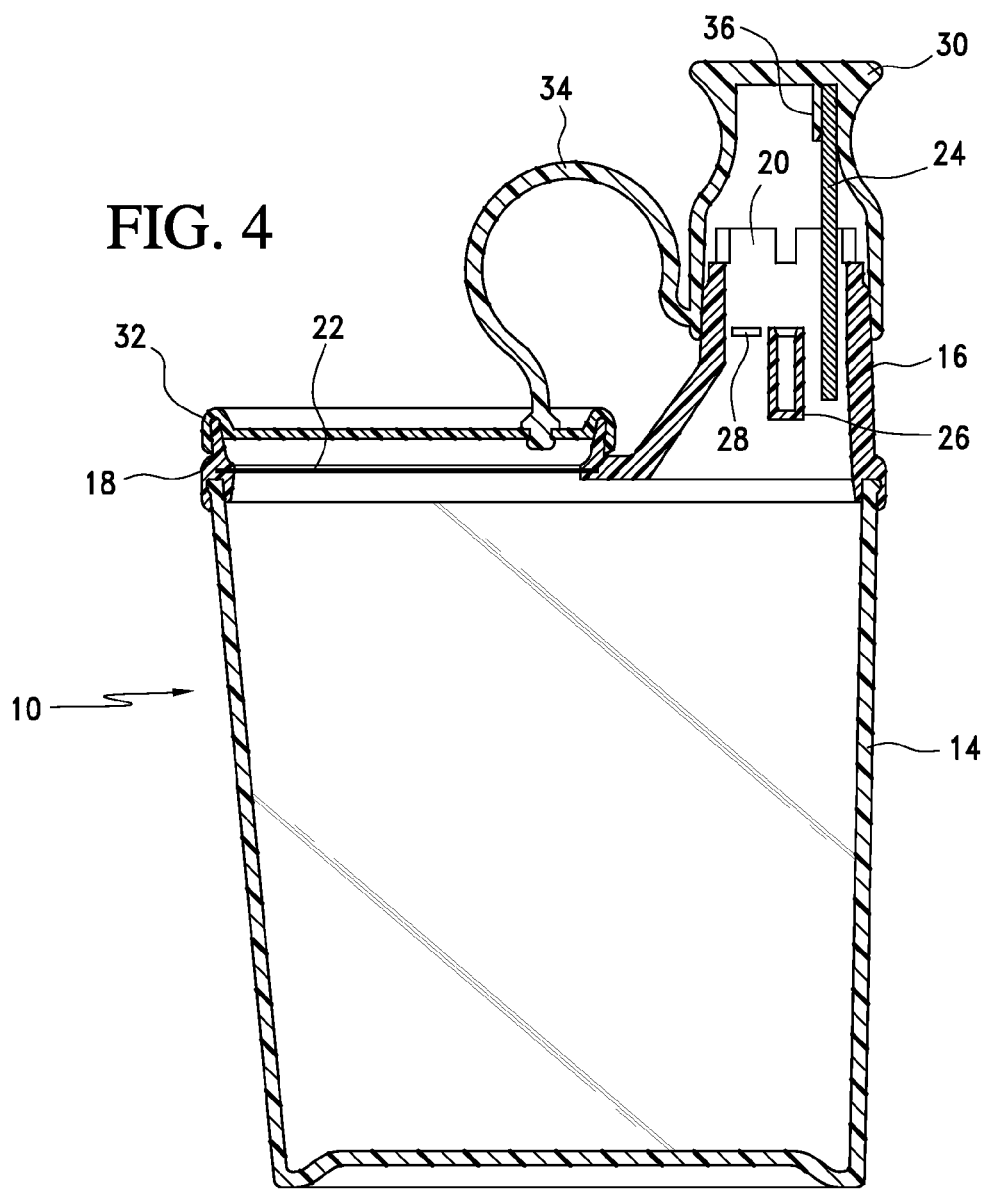
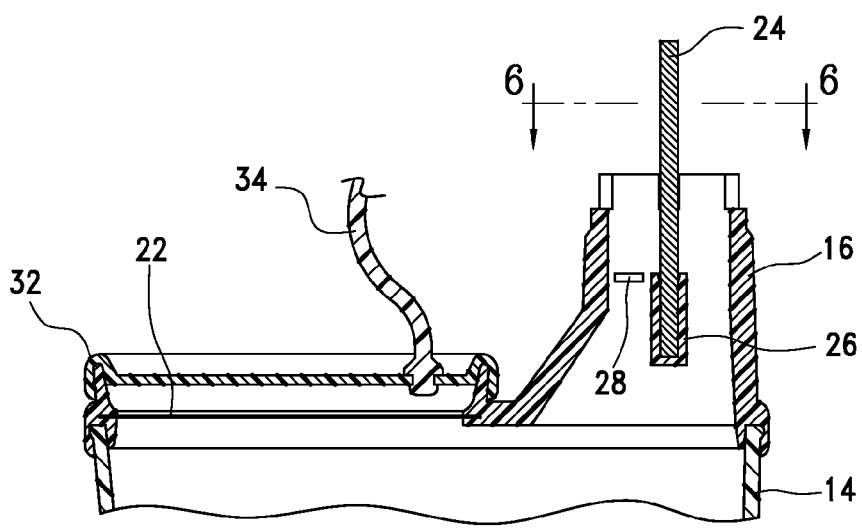

FUEL SAMPLER/STRAINER ASSEMBLY

BACKGROUND OF THE INVENTION

1. Field of the Invention

The present invention relates to hand tools, and more particularly to a fuel checker designed for use in conjunction with fuel tank valves and incorporating a receptacle for receiving a specimen of the fuel tank contents, and returning the specimen to the fuel tank, while filtering water and contaminants from the fuel, and discarding water and contaminants.

2. Description of the Related Art

As a recognized safety precaution, the nature of the fuel in aircraft gas tanks must be checked before each flight to determine the presence of any contaminating agents as well as the octane rating. In the past, this inspection has been effected by, for example, the opening of the tank quick drain valve, by any suitable means in allowing a portion of the fuel to flow outwardly for reception within any convenient type of container. A scrutiny of the withdrawn fuel by an experienced individual will readily indicate whether the fuel is clear or is contaminated, and, further, as to what the octane rating of such fuel might be since its coloration is indicative thereof. In addition to withdrawing a specimen of the fuel from each tank of the aircraft, it is desired that a sample be taken from the lowermost location in the gas system.

Also, the like testing of fuels in the tank of gasoline powered ground vehicles, for example, in the military field, tanks, jeeps, half-tracks, and the like, is a desirable practice for assuming optimum operation. In the past this was accomplished by the use of any convenient instrumentalities, with all the associated inconvenience and time-consumption.

These tasks were made more convenient by the design of more specialized fuel checker devices. U.S. Pat. No. 3,011, 349, issued to D. W. Kratz, entitled "Composite Tool and Receptacle", discloses a tool and receptacle for receiving specimens of aircraft gas tanks. The Kratz device utilizes an elongated body of circular cross-section with a closed lower end. The upper end edge is provided with a series of spaced apart, upwardly opening, generally U-shaped indentations or notches for engaging axially aligned actuating arms of a pet cock type quick drain valve. The elongated body is preferably formed of molded transparent plastic. The device has a screwdriver assembly integral to the bottom end of the elongated body which is handy during various operations typically involved with aircraft maintenance.

Present applicant, Robert M. Brodbeck, is the inventor of an improved fuel checker disclosed and claimed in U.S. Pat. No. 5,359,905, entitled "Fuel Checker For Use With Pet Cock or Ball and Spring Drain Valves." The '905 apparatus comprises an elongated body of substantially circular cross-section. The body is fabricated of transparent molded material and is open at its upper end. The body is of tubular character through a portion of its length for defining a fuel-receiving compartment having a central axis and communicating with the open upper end of the body. The body has spaced-apart indentations in its upper end edge for alignment and cooperation with associated actuating arms of a pet cock drain valve, if such a pet cock drain valve is utilized. The tubular portion is closed at its lower end portion. A resilient semi-rigid rod is removably attached at a first end to the lower end portion of the tubular portion. The resilient rod extends along the central axis beyond the upper end edge of the body so as to engage and manipulate a ball and spring drain valve at a second end of the rod, if such a ball and spring drain valve is utilized. Additionally, the rod is supported at an intermediate portion thereof. Supporting the rod at the first end (lower end) provides much more effective use with ball and spring type drain valves making it much less flimsy and incapable of being pushed down the elongated body during use by the opposing force of the ball and spring valve.

Recently, the Environmental Protection Agency (EPA) has mandated that no fuel can be thrown out onto the tarmac ramp. Therefore, it has become desirable to pour the tested fuel back into the fuel tank. This is undesirable if the sample has water and/or other contaminants. Thus, one desires to filter out such contaminants and return the fuel to the tank.

In response to this problem Wing Aero Products, Inc. distributes what is referred to as "The GATS Jar". The GATS Jar is a stand alone fuel checker/separator device that provides both checking and separation of water and other contaminants. It includes a cap that supports a separator screen that creates a barrier to the passage of water through it and certain particulate debris, but remains no obstacle to the flow of fuel. The GATS Jar; however, has an open end so that while not in use it is difficult to store the device due to the resultant fumes and potential dripping of residual fuel from it. Furthermore, it includes a plastic plunger that makes it less than substantial. Additionally, the GATS Jar has synthetic screen that is susceptible to punctures and tears.

Additionally, present co-applicant, Robert M. Brodbeck, is the co-inventor of an improved filter assembly for a fuel checker disclosed and claimed in U.S. Pat. No. 6,991,724 entitled "Water, Sediment/Fuel Separator for Fuel Checker." The '724 filter assembly includes a filter housing, a removable screen assembly, a first protective cap and a second protective cap. The filter housing includes a fuel receiving end portion and a fuel exiting end portion. The fuel receiving end portion is shaped to securely attach to a fuel checker. The filter housing defines a volume for containing checked fuel. A removable screen assembly is securely attachable to the fuel exiting end portion. The removable screen assembly includes a flexible screen housing and a filter screen supported by the flexible screen housing. The filter screen is a barrier to water and desired particulate debris. A first protective cap fits over the fuel receiving end portion for containing evaporative fumes while the filter assembly is being stored. A second protective cap fits over the removable screen assembly and protects the screen when the filter assembly is being stored.

SUMMARY OF THE INVENTION

In a broad aspect, the present invention is a fuel sampler/strainer for receiving a specimen of the fuel tank contents, and returning the specimen to the fuel tank, while filtering water and contaminants from fuel, and discarding water and contaminants. The fuel sampler/strainer assembly includes a housing formed of fuel resistant material including a transparent elongated main body, a fuel receiving portion at an upper end thereof, and a fuel exiting portion also at the upper end thereof. The elongated main body has a closed lower end. The fuel receiving portion is generally tubular and has spaced-apart indentations in its upper end edge for alignment and cooperation with associated actuating arms of a pet cock drain valve. A rod is removably attachable at a first end to the fuel receiving portion and extends along a central axis of the fuel receiving portion and beyond the upper end edge of the fuel receiving portion so as to engage and manipulate a ball and spring drain valve at a second end of the rod. The fuel exiting portion includes a filter screen functioning as a barrier to water and desired particulate debris. A first protective cap fits over the fuel receiving portion for containing evaporative fumes while the fuel sampler/strainer assembly is being stowed. A second protective cap fits over the fuel exiting portion for similar purposes.

Use of the present invention has several advantages over the GATs Jar. It is compact and therefore can be easily stowed. The housing is of substationally heavier material making it more durable. The rod can be stowed in either the fuel receiving portion or in the cap for the fuel receiving portion. It is entirely sealable when maintained in a stowed mode. Therefore, fumes and residual fuel cannot leak. The fuel sampler/strainer can be supported on the drain tube of a sump with a remote actuating lever. This is particularly adaptable for use on, for example, a Cessna 172N.

BRIEF DESCRIPTION OF THE DRAWINGS

FIG. 4 is a view taken along line 4-4 of FIG. 1, showing the rod in its stowed position.

FIG. 5 is a view taken along line 5-5 of FIG. 2, showing the rod inserted in an operable position.

DETAILED DESCRIPTION OF THE INVENTION

Figures 1, 2, 3:
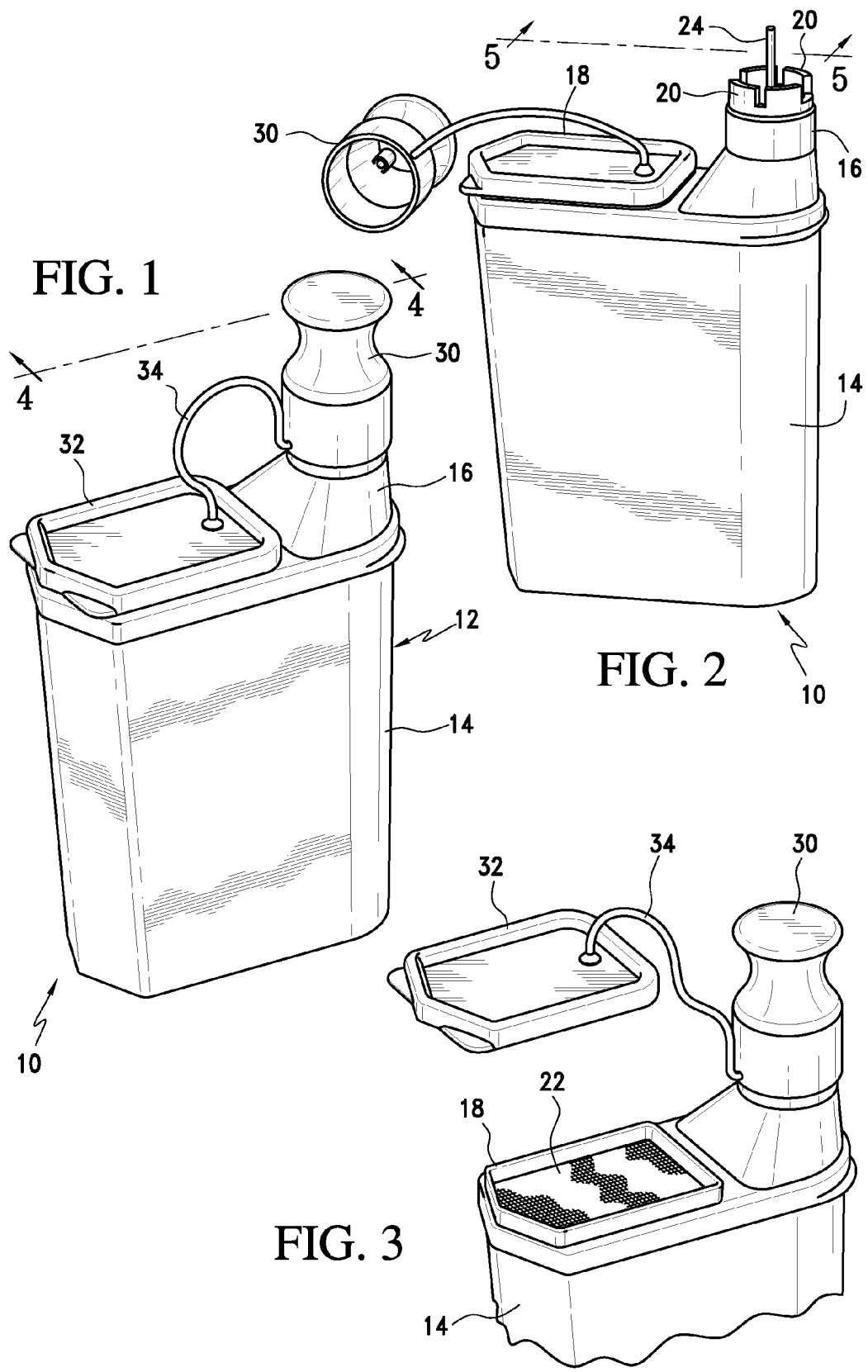
FIG. 1 is a front side perspective view of the fuel sampler/strainer assembly of the present invention.
FIG. 2 is a side perspective view of the fuel sampler/strainer assembly showing the fill valve cap off and the rod in place.
FIG. 3 is a front side perspective view of an upper portion of the fuel sampler/strainer assembly showing the fill valve cap on and the screen cap off.
Figure 6:
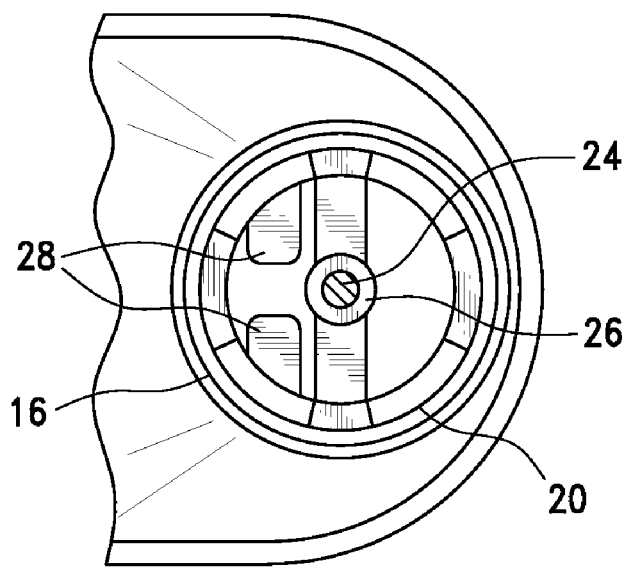
FIG. 6 is a view taken along line 6-6 of FIG. 5.

Referring now to the drawings and the characters of reference marked thereon, FIGS. 1-7 illustrate a preferred embodiment of the fuel sampler/strainer of the present invention, designated generally as 10. The filter assembly 10 includes a housing, designated generally as 12, formed of fuel resistant material. The housing 12 includes a transparent elongated main body 14, a fuel receiving portion 16 at an upper end thereof, and a fuel exiting portion 18 also at the upper end thereof. The fuel exiting portion 18 is spaced from the fuel receiving portion 16. The elongated main body 14 has a closed lower end. The housing 12 preferably includes planar front and back surfaces for optimal stowability.

As can be seen in FIGS. 2 and 4, the fuel receiving portion 16 is of generally tubular character and communicates with the open upper end of the elongated main body 14. The fuel receiving portion 16 has a plurality of spaced-apart indentations 20 in its upper end edge for alignment and cooperation with associated actuating arms of a pet cock drain valve, when such a pet cock drain valve is utilized.

As best seen in FIGS. 3 and 4, the fuel exiting portion 18 includes a filter screen 22 functioning as a barrier to water and desired particulate debris. The filter screen 22 is preferably formed of stainless steel and provides particulate debris filtration to approximately 120 microns. It provides separation of water and other contaminants. In a preferred implementation the filter screen 22 is stainless steel bolting cloth, the mesh is 145 per lineal inch, with a wire diameter of 0.0022 inch, and a width opening of 0.0047 inch, making it very close to a 120 micron filter. The fuel receiving portion 16 and fuel exiting portion 18 are preferably a single integral unit. As such, the filter screen 22 is removable relative to the main body 14 for the purposes of cleaning.

A rod 24 is removably attachable at a first end to a receptacle 26 of the fuel receiving portion 16, as shown in FIG. 5. Thus, when secured in the receptacle 26 the rod 24 extends along a central axis of the fuel receiving portion 16 and beyond the upper end edge of the receiving portion 16 so as to engage and manipulate a ball and spring drain valve (not shown) at a second end of the rod 16, when such a ball and spring drain valve is utilized. The rod 24 is formed of a non-ferrous metal such as brass. It is approximately $3/32$ inches in diameter.

A first protective cap 30, i.e. fill valve cap, fits over the fuel receiving portion 16 for containing evaporative fumes while the fuel sampler/strainer assembly 10 is being stowed. Similarly, a second protective cap 32, i.e. screen cap, fits over the fuel exiting portion 18 and protects the screen and contains evaporative fumes when the fuel sampler/strainer assembly 10 is being stowed.

The caps 30, 32 are preferably connected to each other by a flexible connecting member 34.

The main body 14 of the housing 12 is preferably fabricated of molded plastic material such as cellulose acetate butyrate. The distance from the front panel of the housing 12 and the rear panel of the housing 12 is approximately 2 inches. The distance from one said of the housing 12 to the other side is approximately 4.5 inches. The unitary structure of the fuel receiving portion 16 and fuel exiting portion 18 is preferably formed of a plastic such as polypropylene.

The upper edge of the main body 14 cooperates with the unitary structure of the fuel receiving portion 16 and fuel exiting portion 18 and provides a friction fit therewith.

In use, a fuel sample is checked with the cap 30 off and the cap 32 on. The contents are then poured back into the gas tank with cap 30 on and cap 32 removed. The water and contaminants are then discarded with cap 32 on and cap 30 removed.

The fuel sampler/strainer assembly 10 can be easily stored by connecting the caps 30, 32. Thus, fumes and residual fuel cannot leak. Since the fuel sampler/strainer assembly 10 is relatively narrow it can be conveniently stowed in a seat pocket or side pocket of an airplane.

As shown in FIG. 4, the rod 24 can be stowed in a rod engagement member 36 of the cap 30 when not in use.

Figure 7:
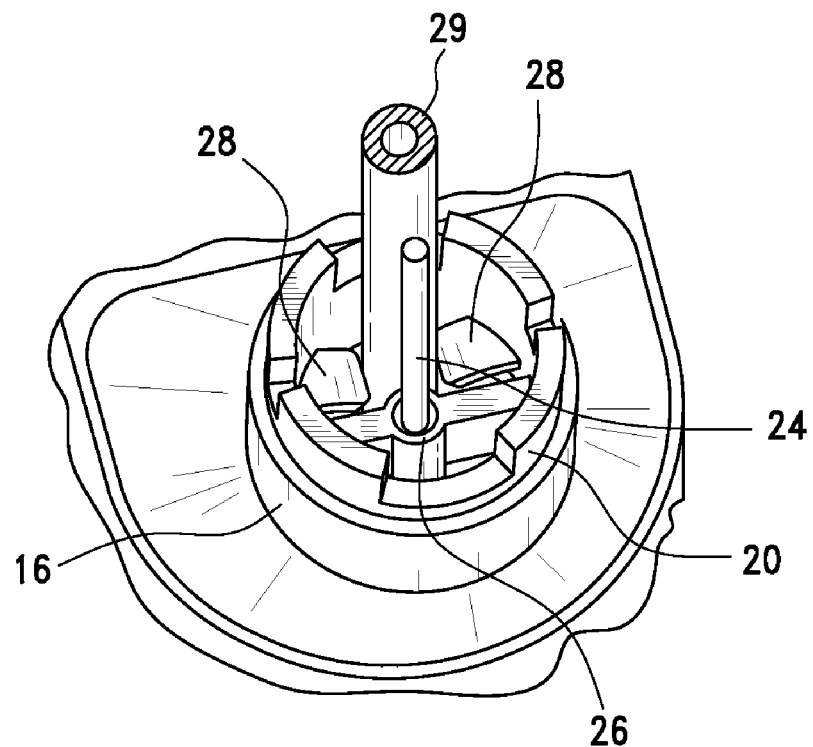
FIG. 7 is a view showing fuel sampler/strainer supported by drain tube gripping flaps on a remotely operated sump drain tube.

As can be seen in FIG. 7, the entire fuel sampler/strainer can be supported from a sump drain tube 29 to allow for a hands free operation of a remote drain lever, by the use of gripping flaps 28 which provide a friction fit relative to the drain tube 29.

Other embodiments and configurations may be devised without departing from the spirit of the invention and the scope of the appended claims.

The invention claimed is:

1. A fuel sampler/strainer assembly for receiving a specimen of the fuel tank contents of a fuel tank and returning the specimen to the fuel tank, said fuel tank of a type having either a ball and spring drain valve or a pet cock drain valve, said fuel sampler/strainer comprising:

a) a housing formed of fuel resistant material, comprising:
   a transparent elongated main body, a fuel receiving portion at an upper end thereof, and a fuel exiting portion also at said upper end thereof non-concentrically spaced from said fuel receiving portion, said elongated main body having a closed lower end, wherein
   i. said fuel receiving portion is of generally tubular character and communicates with the open upper end of said elongated main body, said fuel receiving portion having a plurality of axially extending spaced-apart indentations in its upper end edge for alignment and cooperation with associated actuating arms of a pet cock drain valve, when such a pet cock drain valve is utilized, said fuel receiving portion having a receptacle, and wherein ii. said fuel exiting portion includes a filter screen functioning as a barrier to water and desired particulate debris;

b) a solid rod removably attachable at a first end to said receptacle of said fuel receiving portion and extending along a central axis of said fuel receiving portion and beyond the upper end edge of said fuel receiving portion so as to engage and manipulate a ball and spring drain valve at a second end of said rod, when such a ball and spring drain valve is utilized;

c) a first protective cap for fitting over said fuel receiving portion for containing evaporative fumes while the fuel sampler/strainer assembly is being stowed; and, d) a second protective cap for fitting over said fuel exiting portion and for protecting said screen and containing evaporative fumes when the fuel sampler/strainer assembly is being stowed, wherein said fuel receiving portion comprises drain tube gripping flaps for supporting the fuel sampler/strainer on a remotely actuated sump drain tube.

2. The fuel sampler/strainer assembly of claim 1, wherein first protective cap comprises a rod engagement member for engaging said rod if the rod is not used.

3. The fuel sampler/strainer assembly of claim 1, wherein said rod is formed of a non-ferrous metal.

4. The fuel sampler/strainer assembly of claim 1, wherein said rod is formed of brass material.

5. The fuel sampler/strainer assembly of claim 1, wherein said rod is approximately 3/32 inches in diameter.

6. The fuel sampler/strainer assembly of claim 1, wherein said filter screen is formed of stainless steel.

7. The fuel sampler/strainer assembly of claim 1, wherein said filter screen provides particulate debris filtration to approximately 120 microns to provide separation of water and other contaminants from the fuel being returned to the tank.

8. The fuel sampler/strainer assembly of claim 1, wherein said filter screen is removable for cleaning as a part of a single integral unit comprising said fuel receiving portion and said fuel exiting portion.

9. The fuel sampler/strainer assembly of claim 1, wherein said fuel receiving portion and said fuel exiting portion are a single integral unit.

10. The fuel sampler/strainer assembly of claim 1, wherein said first and said second protective caps are connected to each other by a flexible connecting member.

11. The fuel sampler/strainer assembly of claim 1, wherein said housing includes planar front and back surfaces for optimal stowability.

* * * * *